US009301685B2

(12) United States Patent
Kodama

(10) Patent No.: US 9,301,685 B2
(45) Date of Patent: Apr. 5, 2016

(54) NOTIFICATION APPARATUS, METHOD FOR PERFORMING NOTIFICATION AND ASSIST ROBOT ACTING AS THE SAME

(71) Applicant: TOSHIBA TEC KABUSHIKI KAISHA, Shinagawa-ku, Tokyo (JP)

(72) Inventor: Mina Kodama, Tokyo-to (JP)

(73) Assignee: Toshiba Tec Kabushiki Kaisha, Tokyo (JP)

( * ) Notice: Subject to any disclaimer, the term of this patent is extended or adjusted under 35 U.S.C. 154(b) by 98 days.

(21) Appl. No.: 14/193,108

(22) Filed: Feb. 28, 2014

(65) Prior Publication Data
US 2014/0240106 A1 Aug. 28, 2014

(30) Foreign Application Priority Data

Feb. 28, 2013 (JP) .................................. 2013-039053

(51) Int. Cl.
*A61B 5/00* (2006.01)
*A61G 12/00* (2006.01)
*G08B 1/08* (2006.01)

(52) U.S. Cl.
CPC . *A61B 5/00* (2013.01); *A61G 12/00* (2013.01); *G08B 1/08* (2013.01)

(58) Field of Classification Search
CPC ...................... A61B 5/1115; A61B 2560/0247; A61B 5/0816; A61B 5/6887; A61B 5/6892; A61B 2562/046; A61B 5/0002; A61B 5/0022; A61B 5/01; A61B 5/02; A61B 5/024; A61B 5/02405; A61B 5/1113; A61B 5/1117; G06F 19/3418; G06F 17/50; G06F 19/3406; G06F 19/3462; G06F 2217/04; A61G 2007/0527; A61H 1/00; A61H 1/0262; A61H 2201/1215; A61H 2201/14; A61H 2201/163; A61H 2201/1642; A61H 2201/1659; A61H 2201/5061; A61H 2201/5064; A61H 2201/5092; A61H 2201/5097; A61H 2203/0406; A61H 3/00; A61H 3/008; A63B 2022/0094; A63B 2024/0093; A63B 2071/0655; A63B 21/00178; A63B 21/00181; A63B 2220/54; A63B 2220/805; A63B 2225/20; A63B 2225/50; A63B 23/03541; A63B 23/0405; A63B 23/08; A63B 24/0087; A63B 69/0064; G06N 3/008; G06Q 10/10; G06Q 50/22; H04L 67/12; H04L 67/26
USPC ........................ 340/573.4; 348/E7.077, 14.02
See application file for complete search history.

(56) References Cited

U.S. PATENT DOCUMENTS

2006/0022425 A1* 2/2006 Nishimoto ................. B62J 6/18 280/260
2006/0046548 A1* 3/2006 Nishimoto ................. B62J 6/18 439/244

(Continued)

FOREIGN PATENT DOCUMENTS

JP  2002-143100        5/2002
JP  2006095263 A   *  4/2006

(Continued)

OTHER PUBLICATIONS

First Office Action for Japanese Patent Application No. 2013-039053 Dated Jan. 20, 2015, 6 pages.

*Primary Examiner* — Fekadeselassie Girma
(74) *Attorney, Agent, or Firm* — Amin, Turocy & Watson, LLP

(57) ABSTRACT

In accordance with an embodiment, a notification apparatus comprises a detection module and a notification module. The detection module detects a predetermined operation confirmation sound from a medical instrument. The notification module sends a notification to a predetermined terminal in response to the detection of the operation confirmation sound.

5 Claims, 3 Drawing Sheets

(56) References Cited

U.S. PATENT DOCUMENTS

| | | | |
|---|---|---|---|
| 2007/0037645 A1* | 2/2007 | Ishikawa | B62M 25/08 474/80 |
| 2007/0068332 A1* | 3/2007 | Fujii | B62J 99/00 74/551.8 |
| 2007/0192910 A1* | 8/2007 | Vu et al. | 901/17 |
| 2007/0296176 A1* | 12/2007 | Watarai | B62M 25/08 280/238 |
| 2008/0087126 A1* | 4/2008 | Oda | B62K 23/06 74/473.13 |
| 2008/0087131 A1* | 4/2008 | Tetsuka | B62K 23/02 74/502.2 |
| 2008/0168856 A1* | 7/2008 | Tetsuka | B62K 23/06 74/502.2 |
| 2009/0108782 A1* | 4/2009 | Klatt | H02P 6/001 318/400.17 |
| 2009/0260158 A1* | 10/2009 | Kazuno et al. | 5/600 |
| 2010/0244401 A1* | 9/2010 | Hara | B62M 9/122 280/261 |
| 2011/0156915 A1* | 6/2011 | Brauers et al. | 340/573.4 |
| 2011/0161054 A1* | 6/2011 | Woolf et al. | 703/1 |
| 2012/0056747 A1* | 3/2012 | Stadlthanner et al. | 340/573.4 |
| 2012/0109436 A1* | 5/2012 | Saida | B60L 11/007 701/22 |
| 2012/0143583 A1* | 6/2012 | Huang | G06F 17/5027 703/14 |
| 2012/0310257 A1* | 12/2012 | Kuchenbecker | A61B 19/2203 606/130 |
| 2013/0070044 A1* | 3/2013 | Naidoo et al. | 348/14.02 |
| 2013/0138302 A1* | 5/2013 | Hara | B62J 1/08 701/49 |
| 2013/0139634 A1* | 6/2013 | Tauchi | B62M 25/08 74/473.13 |
| 2013/0168942 A1* | 7/2013 | Musgrove | B62M 9/04 280/210 |
| 2013/0209980 A1* | 8/2013 | Kuchenbecker et al. | 434/262 |
| 2013/0311131 A1* | 11/2013 | Tanaka | B62M 25/04 702/150 |
| 2014/0015659 A1* | 1/2014 | Tetsuka | B62K 23/02 340/432 |
| 2014/0046291 A1* | 2/2014 | Harris | A61M 5/16836 604/503 |
| 2014/0062061 A1* | 3/2014 | Gettings et al. | 280/423.1 |
| 2014/0070930 A1* | 3/2014 | Hara | B62M 25/00 340/432 |
| 2014/0100491 A1* | 4/2014 | Hu et al. | 601/27 |
| 2014/0109718 A1* | 4/2014 | Tan | B62M 25/04 74/523 |
| 2014/0318306 A1* | 10/2014 | Tetsuka | B62M 25/08 74/502.2 |
| 2014/0324581 A1* | 10/2014 | Nordstrom | G06Q 30/0256 705/14.54 |

FOREIGN PATENT DOCUMENTS

| | | |
|---|---|---|
| JP | 2006-202088 | 8/2006 |
| JP | 2007-319287 | 12/2007 |
| JP | 2010-140119 | 6/2010 |
| JP | 2011-045460 | 3/2011 |

\* cited by examiner

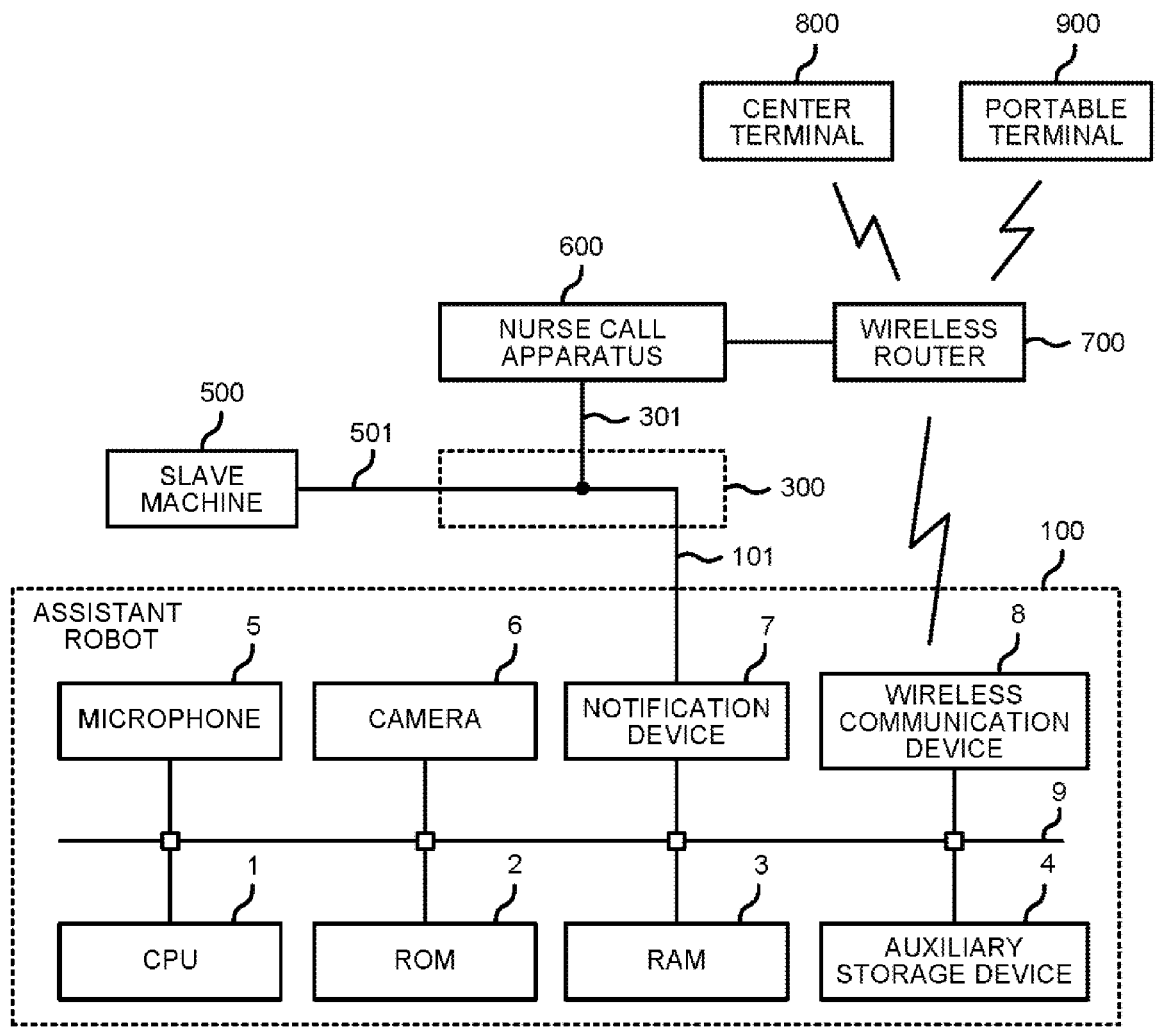

NOTIFICATION APPARATUS, METHOD FOR PERFORMING NOTIFICATION AND ASSIST ROBOT ACTING AS THE SAME

CROSS-REFERENCE TO RELATED APPLICATION

This application is based upon and claims the benefit of priority from Japanese Patent Application No. 2013-039053, filed Feb. 28, 2013, the entire contents of which are incorporated herein by reference.

FIELD

Embodiments described herein relate to a notification apparatus, a method for performing a notification by the notification apparatus and an assist robot which acts as the notification apparatus.

BACKGROUND

There are known a system which can be connected with a medical instrument and automatically notifies a remote terminal of an operation state of the medical instrument, and a medical instrument which automatically notifies a remote terminal of an operation state thereof.

BRIEF DESCRIPTION OF THE DRAWINGS

FIG. 2 is a block diagram illustrating the assist robot shown in FIG. 1;

FIG. 3 is a diagram illustrating an example of the information recorded in an information table.

DETAILED DESCRIPTION

In accordance with an embodiment, a notification apparatus comprises a detection module and a notification module. The detection module detects a predetermined operation confirmation sound from a medical instrument. The notification module sends a notification to a predetermined communication terminal in response to the detection of the operation confirmation sound.

An example of the embodiment is described below with reference to the accompanying drawings. Further, an assist robot capable of functioning as a notification apparatus is exemplarily described in the embodiment.

Figure 1:
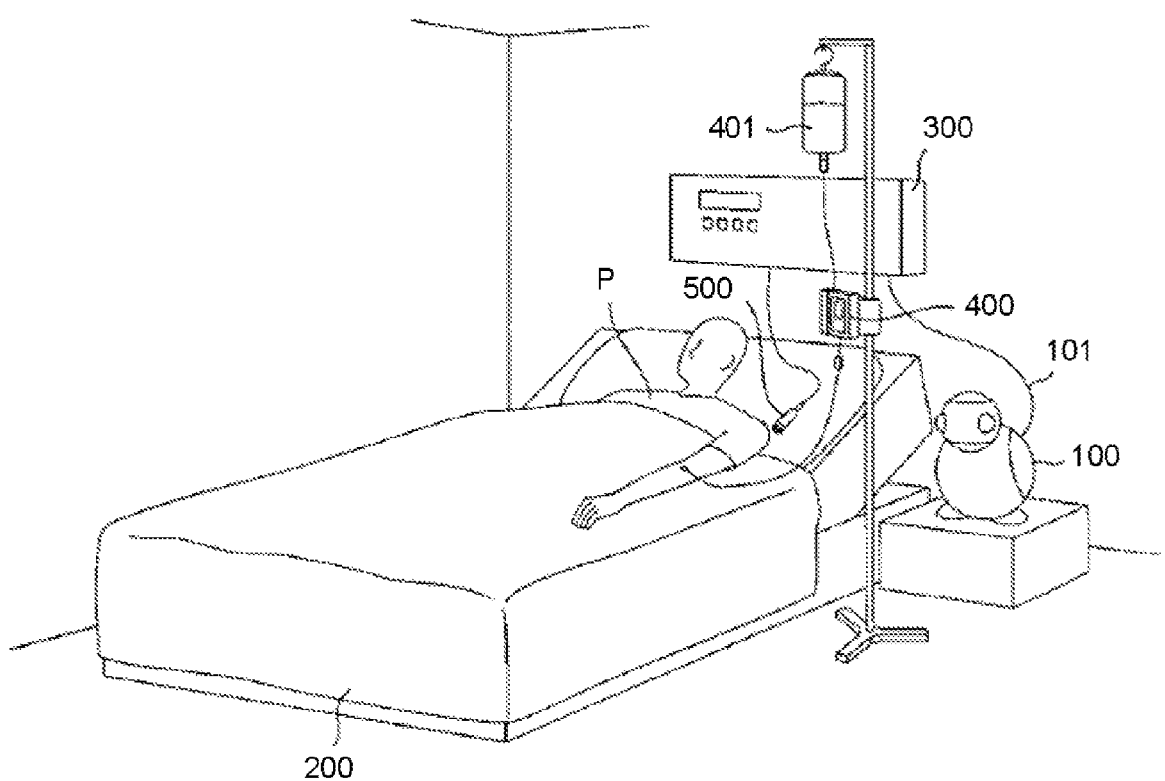
FIG. 1 is an oblique view illustrating an example of the use form of an assist robot according to an embodiment.

FIG. 1 is an oblique view illustrating an example of the use form of an assist robot 100 according to the embodiment.

The assist robot 100 is located nearby a sickbed 200. The assist robot 100 is connected with a bed console unit 300 via a cable 101. The assist robot 100 has a notification function of notifying a remote terminal of the operation state of a medical instrument arranged nearby the sickbed 200. In FIG. 1, an automatic intravenous drip injection apparatus 400 (hereinafter referred to as a "drip injection apparatus") is shown as an example of the medical instrument.

The drip injection apparatus 400 controls the intravenous injection of drips of drug or liquid medicine, stored in a drip bag 401, which is given to a patient P. The drip injection apparatus 400 issues an operation confirmation sound when the operation is completed or failure of the operation occurs.

A slave machine 500 of a nurse call system is arranged nearby the patient P. The slave machine 500 is connected with the bed console unit 300 via a cable 501. The slave machine 500 sends a notification signal through operation of a button.

FIG. 2 is a block diagram illustrating the assist robot 100. In FIG. 2, part of the components of the assist robot 100 is shown while those irrelative to distinctive operations in the embodiment are omitted. Further, in FIG. 2, same numerals are applied to components similar to those shown in FIG. 1.

The assist robot 100 comprises a CPU (central processing unit) 1, a ROM (read-only memory) 2, a RAM (random-access memory) 2, an auxiliary storage device 4, a microphone 5, a camera 6, a notification device 7, a wireless communication device 8 and a bus line 9.

The CPU 1 carries out an information processing according to the operating system and application programs stored in the ROM 2 and the RAM 3 to achieve various functions for providing assistance for the patient P. The information processing includes the notification processing described later for realizing a notification function.

The ROM 2 may store application programs as well as the operating system, if needed. Further, the ROM 2 may also store data to which the CPU 1 refers to carry out various processing.

The RAM 3 stores data to which the CPU 1 refers to carry out various processing. Further, the RAM 3 is used as a so-called work area to store data temporarily used by the CPU 1 to carry out various processing.

The auxiliary storage device 4 is, for example, an HDD (Hard Disk Drive) or an SSD (Solid State Drive) and the like. The auxiliary storage device 4 stores data used by the CPU 1 to carry out various processing or data generated in the processing by the CPU 1. The auxiliary storage device 4 may also store application programs.

The microphone 5 outputs a sound data representing the sounds around the assist robot 100.

The camera 6 captures the image of the surroundings of the assist robot 100 to output the image data as described above. The camera 6 may be, for example, a well-known image capturing device such as a CCD camera. Further, the image data output from the camera 6 may be either of moving images (motion picture) data and still images data.

The notification device 7 sends, under the control of the CPU 1, a notification signal equivalent to a signal sent from the slave machine 500 to the cable 101. The cable 101 is connected with the cable 301 to which a nurse call apparatus 600 is connected in the bed console unit 300. The cable 301 is also connected with the cable 501. Thus, the bed console unit 300 provides, without distinction, the notification signal sent from the notification device 7 and the notification signal sent from the slave machine 500 to the nurse call apparatus 600. Further, the notification device 7 may be externally mounted on the assist robot 100. Thus, the notification device 7 is an example of a transmitting device which sends a notification signal becoming trigger of the notification, that is, a signal for notifying to a predetermined terminal.

The wireless communication device 8 communicates with a wireless router 700, a center terminal 800 and a portable terminal 900. The wireless router 700 is connected with the nurse call apparatus 600. Then, the wireless router 700 properly intermediates the communication among the wireless communication device 8, the nurse call apparatus 600, the center terminal 800 and the portable terminal 900. Thus, the wireless communication device 8 wirelessly communicates with the center terminal 800 and a portable terminal 900 respectively via the wireless router 700.

The nurse call apparatus 600 includes a plurality of ports. In FIG. 1, only the assist robot 100 and the slave machine 500 connected with one port are shown. However, at least one of the assist robot 100 and the slave machine 500 may be properly connected with a plurality of ports, respectively. When one of the plurality of ports receives a notification signal, the nurse call apparatus 600 notifies the center terminal 800 or the portable terminal 900 that a notification is given from a notification source associated with the port. The nurse call apparatus 600 may be an existing apparatus. Further, the nurse call apparatus 600 is also referred to as a nurse call master machine.

The center terminal 800 is arranged at the nurse center and the like in a medical facility. Upon receiving a notice from the nurse call apparatus 600, the center terminal 800 performs an operation for notifying a nurse that it receives the notification. Further, the center terminal 800 displays information sent from the assist robot 100 through the wireless router 700. The center terminal 800 may be an existing device. Only one center terminal 800 is shown in FIG. 1, however, a plurality of center terminals 800 may be arranged in a plurality of nurse centers, respectively. The center terminal 800 may be connected with the nurse call apparatus 600 via a wired line.

The portable terminal 900 is carried by a nurse. Upon receiving a notice from the nurse call apparatus 600, the portable terminal 900 performs an operation for notifying a nurse that it receives the notification. Further, the portable terminal 900 displays information sent from the assist robot 100 through the wireless router 700. The portable terminal 900 may be an existing device. Only one portable terminal 900 is shown in FIG. 1, however, typically, a plurality of portable terminals 900 are carried by a plurality of nurses, respectively.

The aforementioned slave machine 500, nurse call apparatus 600, center terminal 800 and portable terminal 900 constitute a well-known nurse call system.

The bus line 9 is connected in communication each other with the CPU 1, the ROM 2, the RAM 3, the auxiliary storage device 4, the microphone 5, the camera 6, the notification device 7 and the wireless communication device 8.

The assist robot 100 is generally transferred in a state that the notification processing program which describes a notification processing mentioned later is stored in the ROM 2 or the auxiliary storage device 4. However, the assist robot 100 in which the notification processing program is not stored in the ROM 2 or the auxiliary storage device 4 and the notification processing program may be transferred, separately. Moreover, the notification processing program may also be written into the ROM 2 or the auxiliary storage device 4 of the assist robot 100 through operation by a user. The notification processing program may be transferred in such a manner that it is recorded in a removable recording medium such as a magnetic disk, an optical-magnetic disk, an optical disk or a semiconductor memory, or transferred via a network.

Information stored in the ROM 2 or the auxiliary storage device 4 includes an information table in which information for discriminating the operation confirmation sound of a medical instrument is recorded.

FIG. 3 is a diagram illustrating an example of the information recorded in the information table.

The information table shown in FIG. 3 contains at least one data record including information relating to items including 'device name', 'operation state', 'sub-notification destination' and 'sound feature'.

Information 'device name' shows the name assigned to a medical instrument outputting an operation confirmation sound to be recognized. Information 'device state' shows the state of a medical instrument when an operation confirmation sound to be recognized is generated. Information 'sub-notification destination' shows the terminal to which the generation of an operation confirmation sound to be recognized should be notified. Information 'sound feature' shows the feature of an operation confirmation sound to be recognized.

For example, in FIG. 3, the data record shown in the second row shows that the operation confirmation sound to be output has the feature shown by the sound feature information B when a medical instrument shown by a name 'intravenous drip injection device A' is in an abnormal state. Moreover, the data record also shows that in the case in which the aforementioned operation confirmation sound is recognized, information relating to the operation confirmation sound should be notified to the portable terminal 900 the discrimination name of which is 'portable terminal A'.

Next, the operations of the assist robot 100 having the structure mentioned above are described below.

Figure 4:
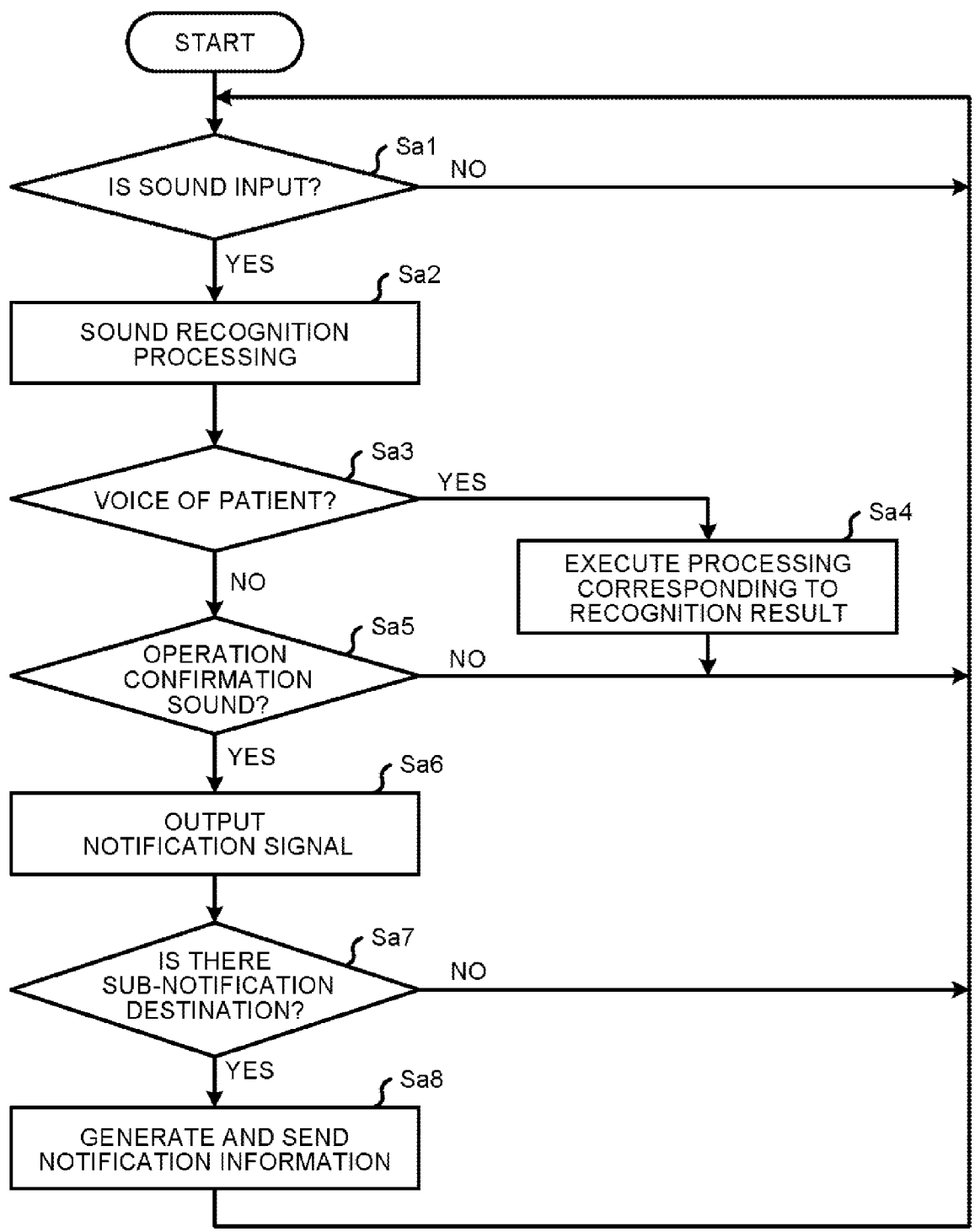
FIG. 4 is a flowchart illustrating a notification processing.

When the assist robot 100 is started, the CPU 1 starts the notification processing shown in FIG. 4 according to a notification processing program stored in the ROM 2 or the auxiliary storage device 4. The content of the processing is described below by way of example, and any other processing capable of achieving the same effect is applicable.

In ACT Sa1, the CPU 1 determines whether or not a sound is input to the microphone 5 based on the sound data output by the microphone 5. If the determination in ACT Sa1 is made that 'no' is taken because no sound is input, the CPU 1 returns to the processing in ACT Sa1. Thus, the CPU 1 waits for the input of a sound into the microphone 5 in ACT Sa1. If the determination in ACT Sa1 is made that 'Yes' is taken because a sound is input, the CPU 1 proceeds to ACT Sa2.

In ACT Sa2, the CPU 1 carries out a sound recognition processing, which may be a well-known one. The sound feature information contained in the information table shown in FIG. 3 is applied to the sound recognition processing described herein. Then, the CPU 1 refers to the sound feature information recorded in the information table to perform recognition on an operation confirmation sound. Thus, the CPU 1 functions as a sound recognition module.

In ACT Sa3, the CPU 1 determines whether or not the voice of a patient P is recognized according to the sound recognition processing in ACT Sa2. If the determination in ACT Sa3 is made that 'YES' is taken because the voice of the patient P is recognized, the CPU 1 proceeds to ACT Sa4.

In ACT Sa4, the CPU 1 executes a control processing for performing an assistant operation corresponding to the recognition result. The CPU 1 controls a device used for carrying out the operation to execute the assistant operation instructed with the voice of the patient P. Then, the CPU 1 returns to the waiting state in ACT Sa1 if the corresponding processing is ended. Thus, the CPU 1 functions as an assistant control module.

If the determination in ACT Sa3 is made that 'No' is taken because no voice of the patient P is recognized according to the sound recognition processing in ACT Sa2, the CPU 1 proceeds to ACT Sa5 from ACT Sa3.

In ACT Sa5, the CPU 1 determines whether or not an operation confirmation sound is recognized according to the sound recognition processing in ACT Sa2. If the determination in ACT Sa3 is made that 'No' is taken because a corresponding operation confirmation sound is not recognized, the CPU 1 returns to the waiting state in ACT Sa1. However, if the determination in ACT Sa5 is made that 'Yes' is taken because a corresponding operation confirmation sound is recognized, the CPU 1 proceeds to ACT Sa6.

As stated above, the CPU 1 discriminates whether the sound represented by the sound data is the sound (voice) of the patient P or an operation confirmation sound, and thus the CPU 1 functions as a discrimination module. Further, the CPU 1 determines whether or not the sound represented by sound data is an operation confirmation sound, and thus the CPU 1 also functions as a determination module. Then, function of a detection is achieved by the CPU 1 acting as a determination module and the microphone 5.

In ACT Sa6, the CPU 1 instructs the notification device 7 to send a notification signal. Thus, the CPU 1 functions as a notification control module. Then, function of a notification module is achieved by the CPU 1 acting as a notification control module and the notification device 7.

The notification device 7 sends a notification signal to the cable 101 in response to the instruction. In this way, the notification signal is transmitted to the nurse call apparatus 600 through the bed console unit 300. The nurse call apparatus 600 notifies the center terminal 800 or the portable terminal 900 that a notification is given from a notification source associated with the port at which the notification signal is received. A terminal to which the nurse call apparatus 600 gives a notification is set in the nurse call apparatus 600 in association with a port beforehand. Upon receiving the notice, the center terminal 800 or the portable terminal 900 carries out an informing operation to inform the occurrence of the notification and the sickbed that generates the notification. Further, if a notification signal sent from the slave machine 500 in response to the operation of the patient P is sent, the nurse call apparatus 600 and the center terminal 800 or the portable terminal 900 also start operation in the way described above. That is, the current informing operation in the terminal informs occurrence of an event that a nurse should hurry to a certain sickbed. The informing operation does not inform the content of the event.

In ACT Sa7, the CPU 1 confirms whether or not a sub-notification destination is set. Specifically, the CPU 1 determines whether or not the data record containing a sound feature information which is used to determine the operation confirmation sound in the sound recognition processing in ACT Sa2 contains a sub-notification destination information. If an operation confirmation sound is determined based on the sound feature information A in the sound recognition processing in ACT Sa2, the CPU 1 determines from the information table shown in FIG. 3 that no sub-notification destination is set. On the other hand, the CPU 1 determines from the information table that a sub-notification destination is set if an operation confirmation sound is determined based on the sound feature information B in the sound recognition processing in ACT Sa2. Afterwards, if the determination in ACT Sa7 is made that 'Yes' is taken because the sub-notification destination is set as described above, the CPU 1 proceeds to ACT Sa8.

In ACT Sa8, the CPU 1 generates a notification information and controls the wireless communication device 8 to send the notification information to the terminal set as the sub-notification destination. The CPU 1 acquires the sound feature information which is used to determine the operation confirmation sound in the sound recognition processing in ACT Sa2 and information of the device name and the operation state thereof contained in the data record. Then, the CPU 1 generates the notification information containing the aforementioned information. The CPU 1 specifies or discriminates at least one of the medical instrument outputting the sound confirmation sound and the operation state indicated with the operation confirmation sound, and thus functions as a specifying module. The wireless communication device 8 sends the notification information, and thus it functions as a sending device. The CPU 1 also functions as a notification control module. Moreover, function of the notification module is achieved by functions of the CPU 1 acting as a notification control module and the wireless communication device 8.

The notification information is sent to the center terminal 800 and the portable terminal 900 via the wireless router 700 and received by the one of the terminals set as the sub-notification destination. The terminal receiving the notification information displays an image showing the information contained in the notification information. If the notification information contains the information including the device name and the operation state of the device, the terminal displays the device name and the operation state thereof. Thus, a person who has the terminal set as the sub-notification destination can confirm the medical instrument, the operation state thereof and the outputted operation confirmation sound caused by the operation state at a location far from the medical instrument.

If the processing in ACT Sa8 is ended, the CPU 1 returns to the waiting state in ACT Sa1. On the other hand, the CPU 1 returns to the waiting state in ACT Sa1 without executing the processing in ACT Sa8 if the determination of ACT Sa1 is made that 'No' is taken because no sub-notification destination is set.

Thus, according to the assist robot 100 of the present embodiment, if a medical instrument has a function of outputting an operation confirmation sound representing an operation state, then a notification can be automatically performed to a nurse call system according to the operation state of the medical instrument. That is, the operation state of a medical instrument which has neither a function of cooperating with a notification apparatus nor an automatic notification function can be automatically notified to a remote terminal.

Then, in the present embodiment, since an existing nurse call system can be used in the notification of the operation state of a medical instrument, existing devices in a medical facility can be used without any changes.

In addition, according to the assist robot 100 of the present embodiment, since a device name and an operation state are determined based on the recognized operation confirmation sound and the notification information indicating the device name and the operation state is sent to a predetermined terminal, a nurse can easily recognize the operation state of a medical instrument at a location remote from the medical instrument.

Further, the assist robot 100 is one which carries out various assistance operations according to the voice (speech) of a patient, but a sound (speech) recognition function for recognizing the voice of the patient can be used to recognize an operation confirmation sound without any modification. For example, a notification processing program may be added to an existing assist robot, and thus, it is easy to realize the assist robot of the present invention.

The embodiment described herein may have the following modifications.

The automatic notification function described herein may be assembled in another unit rather than the assist robot 100, such as the bed console unit 300 and the like or may be achieved as a notification apparatus independent from other apparatus.

In the present embodiment, either of ACT Sa6 and ACT Sa8 (one of notifications in two forms) is carried out to give a notification.

The detection of an operation confirmation sound may be carried out with another method without using a sound or speech recognition technology. For example, an operation confirmation sound may be detected by determining whether or not there is a signal of a predetermined frequency band.

Further, an operation confirmation sound may also be detected if issue of a signal of a predetermined frequency band is maintained for a given time.

Alternatively, a notification may be performed according to the detection of some kind of an operation confirmation sound without distinguishing the type of the operation confirmation sound.

Alternatively, image of the medical instrument captured by the camera 6 may be viewed with the center terminal 800 or the portable terminal 900.

While certain embodiments have been described, these embodiments have been presented by way of example only, and are not intended to limit the scope of the invention. Indeed, the novel embodiments described herein may be embodied in a variety of other forms; furthermore, various omissions, substitutions and changes in the form of the embodiments described herein may be made without departing from the spirit of the invention. The accompanying claims and their equivalents are intended to cover such forms or modifications as would fall within the scope and spirit of the invention.

What is claimed is:

1. A notification apparatus, comprising:
    a detection module configured to detect a predetermined operation confirmation sound from a medical instrument;
    a notification module configured to send a notification to a predetermined terminal in response to the detection of the operation confirmation sound by the detection module;
    a specifying module configured to specify a device name of the medical instrument outputting the operation confirmation sound and an operation state indicated by the operation confirmation sound, based on the operation confirmation sound detected by the detection module; and
    a sending module configured to send notification information to a terminal set as a sub-notification destination if the detection module detects the operation confirmation sound and the sub-notification destination is set, the notification information including information of the device name and the operation state specified by the specifying module.

2. The notification apparatus according to claim 1, wherein the notification module comprises:
    a sending device configured to send a notification signal becoming trigger of the notification in a nurse call system; and
    a notification control module configured to control the sending device to send the notification signal in response to the detection of the operation confirmation sound by the detection module.

3. A notification apparatus, comprising:
    a microphone configured to output a sound data representing sound in surroundings;
    a sending device configured to send a signal for the notification to a predetermined terminal;
    a determination module configured to determine whether or not the sound represented by the sound data is a predetermined operation confirmation sound issued from a medical instrument;
    a notification control module configured to control the sending device to send the signal if the determination module determines that the sound represented by the sound data is the operation confirmation sound;
    a specifying module configured to specify a device name of the medical instrument outputting the operation confirmation sound and an operation state indicated by the operation confirmation sound, based on the operation confirmation sound; and
    a sending module configured to send notification information to a terminal set as a sub-notification destination if the determination module determines that the sound represented by the sound data is the operation confirmation sound and the sub-notification destination is set, the notification information including information of the device name and the operation state specified by the specifying module.

4. A method for performing a notification by a notification apparatus comprising a microphone, a sending device and a transmitting device for sending a signal to notify it to a predetermined terminal, including:
    outputting a sound data indicating a sound in surroundings from the microphone;
    determining whether or not the sound from the microphone is a predetermined operation confirmation sound issued from a medical instrument;
    controlling the transmitting device to send the signal if the sound is the predetermined operation confirmation sound;
    specifying a device name of the medical instrument outputting the operation confirmation sound and in operation state indicated by the operation confirmation sound, based on the operation confirmation sound; and
    controlling the sending device to send notification information to a terminal set as a sub-notification destination if the sound is determined to be the operation confirmation sound and the sub-notification destination is set, the notification information including information of the specified device name and the specified operation state.

5. An assist robot acting as a notification apparatus, comprising:
    a sound recognition module configured to recognize sound in surroundings;
    a discrimination module configured to discriminate whether or not the sound recognized by the sound recognition module is a voice of a person or a predetermined operation confirmation sound from a medical instrument;
    an assist control module configured to control a device used for performing a given operation to assist a person if the discrimination module discriminates that the sound recognized by the sound recognition module is the voice of the person; a notification module configured to send a notification to a predetermined terminal if the discrimination module discriminates that the sound is the operation confirmation sound;
    a specifying module configured to specify a device name of the medical instrument outputting the operation confirmation sound and an operation state indicated by the operation confirmation sound, based on the operation confirmation sound detected by the detection module; and
    a sending module configured to send notification information to a terminal set as a sub-notification destination if the detection module detects the operation confirmation sound and the sub-notification destination is set, the notification information including information of the device name and the operation state specified by the specifying module.

* * * * *